US00PP18907P2

(12) United States Plant Patent
Oud

(10) Patent No.: US PP18,907 P2
(45) Date of Patent: Jun. 10, 2008

(54) ***CALIBRACHOA* PLANT NAMED 'CALUPDAPUVI'**

(50) Latin Name: ***Calibrachoa* sp.**
Varietal Denomination: Calupdapuvi

(75) Inventor: Johannes Simon Nicolaas Oud, Bovenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 31 days.

(21) Appl. No.: 11/639,545

(22) Filed: Dec. 15, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Annette H Para
(74) *Attorney, Agent, or Firm*—S. Matthew Edwards

(57) ABSTRACT

A new *Calibrachoa* plant particularly distinguished by its trailing, outwardly spreading and mounded plant habit, freely branching habit, freely flowering habit, single flowers that are violet in color, and good garden performance.

1 Drawing Sheet

Latin name of the genus and species of the plant claimed: *Calibrachoa* sp.
Varietal denomination: 'Calupdapuvi'.

BACKGROUND OF THE NEW PLANT

The present invention relates to a new and distinct cultivar of *Calibrachoa* plant botanically known as *Calibrachoa* sp. and referred to by the cultivar name 'Calupdapuvi.'

The new *Calibrachoa* is the product of a planned breeding program conducted by the inventor in Enkhuizen, Netherlands. The new *Calibrachoa* cultivar is freely flowering with trailing and spreading plant habit and attractive leaf and flower coloration.

The new *Calibrachoa* originated from a cross-pollination made by the inventor in July 2003 of the *Calibrachoa* sp. variety 'KLEC02073,' not patented, as the female, or seed parent, with a proprietary selection of *Calibrachoa* sp. identified as code number 'Z4012,' not patented, as the male, or pollen parent. The new *Calibrachoa,* was selected as a single plant from the resulting progeny of the cross-pollination in a controlled environment in Enkhuizen, Netherlands in May 2004.

Asexual reproduction of the new cultivar by terminal vegetative cuttings since August 2004, in Enkhuizen, Netherlands has shown that the unique features of this new *Calibrachoa* are stable and reproduced true to type in successive generations.

SUMMARY OF THE INVENTION

Plants of the cultivar 'Calupdapuvi' have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Calupdapuvi.' These characteristics in combination distinguish 'Calupdapuvi' as a new and distinct cultivar:

1. Trailing, outwardly spreading and mounded plant habit
2. Freely branching habit 3. Freely flowering habit
4. Single flowers with violet flower color
5. Good garden performance In side-by-side comparisons conducted in Enkhuizen, Netherlands, plants of the new *Calibrachoa* differed from plants of the female parent selection in the following characteristic:

1. Flowers of the new *Calibrachoa* have a violet color RHS 83B whereas flowers of the female parent selection are dark red about RHS 45B.

In side-by-side comparisons conducted in Enkhuizen, Netherlands, plants of the new *Calibrachoa* differed from plants of the male parent selection in the following characteristic:

1. Plants of the new *Calibrachoa* have are mounded habit whereas the habit of the male parent selection is very trailing.

TABLE 1

DIFFERENCES BETWEEN THE NEW CULTIVAR 'CALUPDAPUVI' AND A SIMILAR CULTIVAR

| | 'Calupdapuvi' | Super Bells Blue 'USCALI51' (U.S. Plant Patent No 14,874) |
|---|---|---|
| Flower color | Colder blue color (83B) | Warmer color (N81A) |
| Leaves | Longer and broader | Smaller, shorter and narrower |

DESCRIPTION OF THE DRAWING

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Calibrachoa.*

DESCRIPTION OF THE NEW CULTIVAR

The observations and measurements described plans grown in Enkhuizen, The Netherlands, practice circumstances outdoor in window boxes during the Summer with day temperatures ranging from 14 to 30° C., night temperatures ranging from 10 to 20° C. Plants used for the photographs and description were about 10 weeks from plants rooted cuttings.

In the following description, color references are made to The Royal Horticultural Society Colour Chart, 2001 Edition, except where general terms of ordinary dictionary significance are used.

The plant:

*Classification.*—Botanical: *Calibrachoa* sp.

Parentage:

*Female parent.*—*Calibrachoa* sp. variety 'KLEC02073,' not patented.

*Male parent.*—Proprietary selection of *Calibrachoa* sp. identified as code number 'Z4012,' not patented.

Propagation:

*Type cutting.*—Terminal vegetative cuttings.

*Time to initiate roots.*—Summer and Winter: About 12 days at 20° C.

*Time to develop roots, summer.*—About 21 days at 20° C.

*Time to develop roots, winter.*—About 28 days at 16° C.

*Root description.*—Fine, fibrous, white in color.

*Rooting habit.*—Freely branching.

Plant description:

*Form.*—Annual flowering plant; indeterminate; initially upright, then trailing and outwardly spreading; uniformly mounded plant form. Freely branching habit; about six to eight basal branches each with about six to eight lateral branches. Pinching enhances development of lateral branches.

*Usage.*—Appropriate for hanging baskets, window boxes, patio containers, and landscapes applications.

*Plant height* (*from soil level to top of plant plane*).—About 15 cm.

*Plant diameter* (*from soil level to lateral branches apices*).—About 70 cm.

*Vigour.*—Vigorous; rapid growth rate.

The stem:

*Main branches, length.*—About 40 cm.

*Main branches, diameter.*—About 2 mm.

*Lateral branches, length.*—About 15 cm.

*Lateral branches, diameter.*—About 1.2 mm.

Internodes:

*Length.*—2 cm.

*Texture.*—Slightly pubescent.

*Strength.*—Strong. Wiry.

*Color.*—144A with some anthocyanin N187A.

The foliage:

*Arrangement.*—Alternate before flowering; opposite after flowers develop; simple; sessile.

*Length.*—About 3.3 cm.

*Width.*—About 1 cm.

*Shape.*—Oblanceolate to elliptic.

*Apex.*—Obtuse.

*Base.*—Attenuate.

*Margin.*—Entire.

*Aspect.*—Mostly flat.

*Texture, upper and lower surfaces.*—Pubescent.

*Venation pattern.*—Pinnate.

*Color.*—Developing foliage, upper surface: 137B. Developing foliage, lower surface: 137C. Fully expanded foliage, upper surface: 137A, midvein 137B, lateral veins similar to lamina. Fully expanded foliage, lower surface: 137B, midvein 137C, lateral veins similar to lamina.

The inflorescence:

*Flower type and habit.*—Single salver form flowers; flowers face mostly upright or outward; axillary. Freely flowering habit.

*Natural flowering season.*—Long day responsive; long flowering period, spring until frost in the autumn; flowering continuous during this period. Plants start flowering about nine weeks after planting rooted cuttings.

*Flower longevity on the plant.*—About seven to ten days.

Flower size:

*Diameter.*—About 2.8 cm.

*Depth* (*height*).—About 2.7 cm.

*Tube length.*—About 1.5 cm.

*Throat diameter, distal end.*—About 7 cm.

*Tube diameter, proximal end.*—About 2 mm.

Flower buds:

*Length.*—About 1.8 cm.

*Diameter.*—About 4 mm.

*Shape.*—Oblong.

*Color.*—Towards the base: N144D. Mid-section: 153D. Towards the apex: 79B.

Petals:

*Arrangement/appearance.*—Single whorl of five petals fused into flared trumpet.

*Length from throat.*—About 1.3 cm.

*Width.*—About 1.3 cm.

*Shape.*—Roughly spatulate with a rounded apex.

*Margin.*—Entire.

*Texture, upper and lower surfaces.*—Smooth, glabrous, satiny.

*Color.*—When opening, upper surface: 86A. When opening, lower surface: 83B. Fully opened, upper surface: N87A. Circumorbital ring: Darker than 79A. Venation, upper surface: 86A. Fully opened, lower surface: N87B. Venation, lower surface: 86A. Flower throat (inside): 7B. Venation, throat: 84A. Flower tube (outside): 1C. Venation, tube: 84A.

Sepals:

*Arrangement/appearance.*—Single whorl of five sepals fused at base, star-shaped.

*Length.*—About 1.3 cm.

*Width.*—About 2.5 mm.

*Shape.*—Lanceolate.

*Apex.*—Acute.

*Margin.*—Entire.

*Texture, upper and lower surfaces.*—Pubescent.

*Color, upper and lower surfaces.*—146A.

Peduncles:

*Length.*—About 1 cm.

*Width.*—About 1 mm.

*Strength.*—Flexible, wiry.

*Texture.*—Pubescent.

*Color.*—144A with some anthocyanin N187A.

Reproductive organs:

*Stamens, quantity per flower.*—Five.

*Anther shape.*—Four-parted, ovate.

*Anther length.*—About 1.2 mm.

*Anther diameter.*—About 1.1 mm.

*Filament length.*—About 6 mm.

*Filament color.*—145C.

*Anther color.*—9C.
*Pollen amount.*—Moderate.
*Pollen color.*—9C.
*Pistils, quantity per flower.*—One.
*Pistil length.*—About 9 mm.
*Stigma shape.*—Ovate.
*Stigma color.*—144B.
*Style length.*—About 7 mm.
*Style color.*—145B.
*Ovary color.*—154C; Apex 83C.

Seed development: Seed development has not been observed to date.

Disease and pest resistance: Plants of the new *Calibrachoa* have not been noted to be resistant to pathogens or pests common to *Calibrachoa*.

Garden performance: Plants of the new *Calibrachoa* have been observed to have good garden performance. Plants of the new *Calibrachoa* have been noted to tolerate rain, wind, and temperatures from 0 to 30° C.

What is claimed is:

1. A new and distinct variety of *Calibrachoa* plant, substantially as illustrated and described herein.

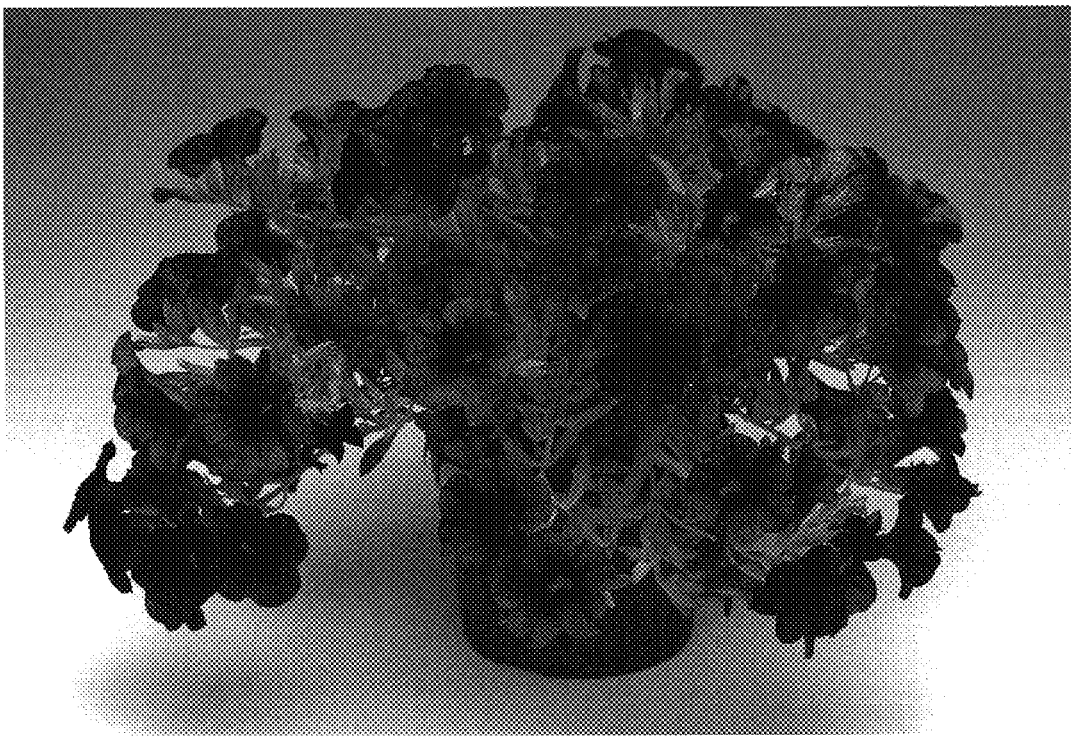

* * * * *